United States Patent [19]

Jongsma

[11] 4,205,184

[45] May 27, 1980

[54] METHOD FOR PROCESSING A TAR CONTAINING BENZYL BENZOATE

[75] Inventor: Cornelis Jongsma, Geleen, Netherlands

[73] Assignee: Stamicarbon, B.V., Geleen, Netherlands

[21] Appl. No.: 864,722

[22] Filed: Dec. 27, 1977

[30] Foreign Application Priority Data

Dec. 28, 1976 [NL] Netherlands .......................... 7614458

[51] Int. Cl.$^2$ .................... C07C 63/08; C07C 103/22; C07C 31/16
[52] U.S. Cl. .................................... 562/494; 568/810; 568/332; 568/324
[58] Field of Search ........................ 260/515 R, 558 R; 560/106; 562/409, 414, 494; 568/800, 802, 810

[56] References Cited

U.S. PATENT DOCUMENTS

| | | | |
|---|---|---|---|
| 2,317,455 | 4/1943 | Gubelmann et al. | 562/494 |
| 2,317,455 | 4/1940 | Gubelmann | 562/494 |
| 2,749,363 | 6/1956 | Williamson et al. | 562/494 |
| 2,785,199 | 3/1957 | Himel | 562/494 |
| 2,813,119 | 11/1957 | Taves | 560/106 |
| 2,843,627 | 7/1958 | Miller et al. | 562/494 |
| 3,235,588 | 2/1966 | Weaver | 562/494 |
| 3,309,289 | 3/1967 | Messina et al. | 562/414 |
| 3,538,165 | 11/1970 | Kahn | 560/106 |
| 3,867,439 | 2/1975 | Hills | 562/414 |
| 3,956,404 | 5/1976 | Walling et al. | 560/106 |
| 4,092,353 | 5/1978 | Wolf | 562/414 |

OTHER PUBLICATIONS

Kirk-Othmer, "Encyclopedia of Chemical Technology," 2nd Ed., 1966, (Interscience Publisher) vol. 8, pp. 368-369, 719 and 761, and vol. 7, p. 204.
Handbook of Chemistry and Physics, published by the Chemical Rubber Company, 46th Ed., 1966, pp. C-180, C-181, C-325 and C-577.

Primary Examiner—J. E. Evans
Assistant Examiner—L. Hendriksen
Attorney, Agent, or Firm—Cushman, Darby & Cushman

[57] ABSTRACT

A method for processing a tar which is formed during the oxidation of an alkyl-benzene compound and which contains substituted or unsubstituted benzyl benzoate, which method comprises the steps of subjecting the tar to either hydrolysis or ammonolysis and then extracting the reaction mixture which is formed from the hydrolysis or ammonolysis. The extracting agent is organic and causes the reaction mixture to separate into liquid phases. The liquid phases are then separated for further processing.

10 Claims, No Drawings

METHOD FOR PROCESSING A TAR CONTAINING BENZYL BENZOATE

The invention relates to a method for processing a tar containing benzyl benzoate.

Mixtures of this type may form in the oxidation of monoalkyl benzene compounds with a gas containing molecular oxygen. The oxydation of toluene is applied on a technical scale, and the benzyl benzoate that may form then is the unsubstituted benzyl benzoate, i.e. that both benzene rings of the benzyl benzoate are unsubstituted. Because of the technical importance the invention will be explained mainly with reference to the toluene oxidation and the tar then obtained, which contains unsubstituted benzyl benzoate.

The invention may also be used, however, for tar that contains substituted benzyl benzoates and which may form, for instance, in the oxidation of other alkyl-benzene compounds.

The oxidation reaction may take place either in the liquid phase with, e.g., a cobalt and/or manganese salt that is soluble in the reaction medium as a catalyst, or in the gaseous phase with, e.g., a catalyst based on an oxide of vanadium or another transition metal (Stanford Research Institute (SRI)-reports No. 7 (1965), 29; No. 7A (1968), 241; No. 7B (1976), 53).

All or part of the benzoic acid, together with all products with lower boiling points may be distilled from the reaction mixture, which contains benzoic acid, benzyl benzoate, other products with higher boiling points than benzoic acid and here referred to by the name of 'tar residue', unconverted toluene and by-products with lower boiling points than benzoic acid, such as benzyl alcohol and benzaldehyde, and the distillate may be processed further for pure benzoic acid so that a tar containing benzyl benzoate and, possibly, some benzoic acid is left as a residue. This residue can be used as the starting material for the method according to the invention.

A tar containing benzyl benzoate which may also be used as the starting material for the method according to the invention can also form if the abovementioned distillate is heated whether or not in the presence of an esterification/re-esterification catalyst, e.g. sulphuric acid, phosphoric acid, borotrifluoride or zinc acetate, in order to esterify or re-esterify benzyl alcohol and/or light benzyl esters, such as benzyl formiate and benzyl acetate, into benzyl benzoate, especially if the mixture still contains benzaldehyde during this esterification.

It is particularly difficult to recover useful products from such tar containing benzyl benzoate. What can be done is not distil benzyl benzoate from the tar residu, but a pure benzyl-benzoate product can hardly be obtained in this way. Applicant has found that the fluorenone component of the tar presents special problems. For, it appears that fluorenone can hardly be separated from benzyl benzoate. But besides fluorenone, other unidentified compounds may play a part.

According to the invention a tar containing benzyl benzoate is processed by subjecting it to a hydrolysis or ammonolysis reaction. Thus the benzyl benzoate with a high boiling point which is difficult to separate from some tar components by distillation is converted into the benzyl alcohol with a considerably lower boiling point in addition to the benzoic acid or a salt or amide thereof, which differs considerably in chemical properties from the benzyl benzoate and the tar components.

Pure benzyl alcohol can be recovered from the hydrolysed or ammonolysed mixture, e.g., by distillation. Benzyl alcohol is a useful product that is used in the scents and flavours industries. Hence, it is achieved by the method according to the invention that a waste product with no applications so far is converted into a useful product.

The hydrolysis of the tar can be effected by means of a basic solution, particularly an aqueous sodium hydroxide solution or a soda solution. Also potassium hydroxide, for instance, or calcium hydroxide might be used. But there is mainly a need of sodium benzoate as a reaction product, so that the hydrolysis is preferably effected with a basic sodium compound. The benzoate salt obtained can be separated from the tar by extraction with water. Instead of hydrolysis, ammonolysis may be used, e.g. with ammonia, liquid ammonia, or, if so desired, an amine, which, preferably, has a boiling point at atmospheric pressure of at most 150° C.

If so desired, the benzoate salt or benzamide thus obtained can be converted into very pure free benzoic acid by reaction with a strong acid, e.g. sulphuric acid or nitric acid.

If so desired, the hydrolysis reaction may also be effected by means of an acid, instead of a basic catalyst, e.g. a mineral acid, such as sulphuric acid or phosphoric acid. Naturally, free benzoic acid will then form, which, if so desired, may be recovered by distillation or by extraction, e.g., be means of water.

The temperature in the hydrolysis or ammonolysis may range, e.g., between 30° and 200° C. The pressure is not critical and preferably ranges between 1 and 10 atm for practical reasons.

Unfortunately, it is extremely difficult to recover not only the benzyl alcohol, but also the benzoate salt, especially the useful sodium benzoate, in a pure form from the reaction mixture obtained in the basic hydrolysis of the benzyl benzoate/tar mixture. Some components of the tar persistently combine with the sodium benzoate, especially in the presence of benzyl alcohol.

According to the invention this problem is solved by extracting the hydrolysis reaction mixture with an organic extracting agent which causes separation into liquid phases with the hydrolysis reaction mixture. In this separation the benzyl alcohol and the tar components pass into the organic phase, while the aqueous phase is a virtually pure sodium-benzoate solution from which solid pure sodium benzoate can be recovered in a simple way. Pure benzyl alcohol and the extracting agent can be recovered from the organic phase by distillation.

Examples of suitable organic extracting agents are aliphatic, aromatic and mixed aliphatic-aromatic hydrocarbons with, preferably, at most 12 carbon atoms per molecule, ethers, esters, and halogenated and, especially, chlorinated or brominated hydrocarbons with normal boiling points, preferably not exceeding 250° C. Specific examples are gasoline, heptane, benzene, toluene, the xylenes, diisopropyl ether, amyl acetate, ethyl benzoate, chloroform, 1,2-dichlorethene, and 1,1,1-trichlorethane. Special preference is given to toluene, as it is available in large quantities in a toluene-oxidation works and effects proper separation.

According to a suitable embodiment of the method according to the invention, the product mixture of the hydrolysis reaction is fed to an extraction column, to which the extracting agent is also fed.

It is also possible for the extracting agent to be present during the hydrolysis reaction. In this case it is recommendable, of course, to choose an extracting agent that is inert under the reaction conditions concerned. After the reaction the product mixture is then separated into an organic layer containing benzyl alcohol, tar residue, and extracting agent and an aqueous layer containing sodium benzoate.

The hydrolysis may then be effected in an extraction column through which the tar containing benzyl benzoate and the basic solution are passed in counter-current relation to the extracting agent.

The invention will be elucidated with reference to the following non-restricting example.

EXAMPLE

The liquid reaction product of the oxidation of toluene in the liquid phase with air in the presence of cobalt acetate as a catalyst (degree of conversion of toluene about 20% by weight) is distilled until virtually all benzoic acid and components with lower boiling points have been removed from the reaction product. The residue is subjected to film evaporation at a temperature of 260° C. and a pressure of 25 mm of Hg. An aqueous sodium hydroxide solution (14% by weight of NaOH) is added to the distillate obtained in the film evaporation, a mixture of benzyl benzoate and tar, in an hydrolysis reactor consisting of a glass flask with reflux condenser and stirring mechanism. The composition of the mixture thus obtained is given in Table I ('before hydrolysis'). The tar residue consists, i.a., of fluorenone (about 40% by weight relative to the tar), 1,2-diphenyl ethane, and 2-methyl, 3-methyl and 4-methyl diphenyls.

The mixture in the hydrolysis reactor is stirred at 100° C. for 30 minutes, after which virtually all benzyl benzoate has been hydrolysed. The composition of the reactor contents after hydrolysis is also given in Table I.

Table I

|  | composition before hydrolysis (% by weight) | composition after hydrolysis (% by weight) |
| --- | --- | --- |
| benzoic acid | 8.7 | — |
| benzyl benzoate | 26.1 | <0.01 |
| tar residue | 8.7 | 8.7 |
| sodium hydroxide | 8.1 | 0.3 |
| water | 48.4 | 49.8 |
| benzyl alcohol | — | 13.3 |
| sodium benzoate | — | 27.9 |

The contents of the hydrolysis reactor are extracted four times with equal portions of toluene (the total amount is equal to twice the weight of water present). The layers of toluene thus obtained are added together and are washed with water (10% by weight relative to the amount of toluene present). After separation of the layers, the washing water is added to the abovementioned aqueous layer.

The toluene and the water are distilled at atmospheric pressure from the washed toluene layer. Next, the residue is distilled at 70° C. and 1 mm of Hg. The top flow of this distillation consists of virtually pure benzyl alcohol (purity over 99% by weight). The residue of the distillation has a composition as mentioned in Table II.

Table II

|  | composition (% by weight) |
| --- | --- |
| fluorenone | 38.9 |
| remaining tar residue | 57.8 |
| benzyl alcohol | 3.3 |
| benzyl benzpate | 0.1 |

The yield of benzyl alcohol after distillation relative to benzyl benzoate is over 99%.

Solid sodium benzoate is obtained virtually quantitatively from the combined water layer by removal of water.

I claim:

1. Method for processing a tar consisting essentially of a benzyl benzoate and tar residue which is formed during the oxidation of an alkyl-benzene compound and which contains substituted or unsubstituted benzyl benzoate, comprising the steps of
   (a) subjecting said tar which contains substituted or unsubstituted benzyl benzoate to a hydrolysis reaction, said reaction effected by means of sufficient aqueous basic solution, or an acid, or by using an acid ion exchange catalyst, at a temperature between about 30° C. and about 200° C. to convert essentially all of said benzyl benzoate to the corresponding benzyl alcohol and the corresponding benzoic acid or benzoate salt and provide a hydrolysis reaction mixture comprising an aqueous phase,
   (b) contacting said hydrolysis reaction mixture with sufficient organic extracting agent having 12 at most carbon atoms per molecule to cause said reaction mixture to separate into liquid phases, and to extract essentially all of the organic material except said benzoic acid or benzoate salt into the organic phase, and
   (c) separating said liquid phases for further processing.
2. Method for processing a tar consisting essentially of a benzyl benzoate and tar residue which is formed during the oxidation of an alkyl-benzene compound and which contains substituted or unsubstituted benzyl benzoate, comprising the steps of,
   (a) subjecting said tar which contains substituted or unsubstituted benzyl benzoate to an ammonolysis reaction, said ammonolysis reaction effected by means of sufficient ammonia, or liquid ammonia, or an amine, at a temperature between about 30° C. and about 200° C. to convert essentially all of said benzyl benzoate to the corresponding benzyl alcohol and the corresponding benzoic acid amide and provide an ammonolysis reaction mixture,
   (b) contacting said ammonolysis reaction mixture with an organic extracting agent having at most 12 carbon atoms per molecule to cause said reaction mixture to separate into liquid phases, and to extract essentially all of the organic material except said benzoic acid amide into the organic phase, and
   (c) separating said liquid phases for further processing.
3. Method for processing a tar consisting essentially of benzyl benzoate and tar residue which is formed during the oxidation of toluene and which contains benzyl benzoate, comprising the steps of,
   (a) reacting said tar containing benzyl benzoate with sufficient aqueous solution of sodium hydroxide or sodium carbonate at a temperature between about 30° C. and about 200° C. to convert essentially all of the benzyl benzoate to benzyl alcohol and sodium benzoate and provide an aqueous hydrolysis reaction mixture, (b) extracting said hydrolysis mixture with sufficient toluene, (c) separating the toluene to extract essentially all of the organic material except sodium benzoate extract phase from the remaining aqueous phase, (d) washing said toluene extract phase with water, (e) adding the washing water to said aqueous phase for further processing of the combined aqueous layer for the sodium benzoate value therein, (f) distilling off the toluene and water still present from the washed toluene extract phase, and (g) distilling the residue of the distillation of step (f) to obtain substantially pure benzyl alcohol.

4. Method according to claim 1 or claim 2, wherein substituted or unsubstituted benzyl alcohol is recovered from the separated liquid phases.

5. Method according to claim 1 wherein the hydrolysis reaction is effected with sodium-hydroxide or sodium carbonate and sodium benzoate is recovered from the separated liquid phases.

6. Method according to claims 1 or 2, wherein the organic extracting agent is toluene.

7. Method according to claim 1 wherein the hydrolysis reaction is carried out in the presence of the extracting agent.

8. Method according to claim 1 wherein said hydrolysis reaction mixture comprises an aqueous phase and an organic phase.

9. Method according to claim 2 wherein said ammonolysis reaction mixture comprises an aqueous phase and an organic phase.

10. Method according to claim 3 wherein said hydrolysis reaction mixture comprises an aqueous phase and an organic phase.

* * * * *

UNITED STATES PATENT AND TRADEMARK OFFICE
CERTIFICATE OF CORRECTION

PATENT NO. : 4,205,184
DATED : May 27, 1980
INVENTOR(S) : Cornelis Jongsma

It is certified that error appears in the above—identified patent and that said Letters Patent is hereby corrected as shown below:

Column 4, line 32, delete "12"; in line 33, insert --12-- after "most".

Column 5, line 6, after "toluene" insert --to extract essentially all of the organic material except sodium benzoate--.

Column 5, lines 9 and 10, delete "to extract essentially all of the organic material except sodium benzoate".

Signed and Sealed this

Sixteenth Day of September 1980

[SEAL]

Attest:

SIDNEY A. DIAMOND

Attesting Officer     Commissioner of Patents and Trademarks